US012754176B2

(12) United States Patent
Huang

(10) Patent No.: US 12,754,176 B2
(45) Date of Patent: Oct. 6, 2026

(54) GAS SAMPLING MECHANISM AND GAS ANALYSIS DEVICE HAVING THE SAME

(71) Applicant: TRIPLE WIN TECHNOLOGY(SHENZHEN) CO.LTD., Shenzhen (CN)

(72) Inventor: Po-Hsiang Huang, New Taipei (TW)

(73) Assignee: TRIPLE WIN TECHNOLOGY(SHENZHEN) CO.LTD., Shenzhen (CN)

( * ) Notice: Subject to any disclaimer, the term of this patent is extended or adjusted under 35 U.S.C. 154(b) by 946 days.

(21) Appl. No.: 18/093,795

(22) Filed: Jan. 5, 2023

(65) Prior Publication Data

US 2024/0053315 A1 Feb. 15, 2024

(30) Foreign Application Priority Data

Aug. 9, 2022 (CN) ......................... 202210947933.6

(51) Int. Cl.
*G01N 33/00* (2006.01)
*G01F 3/22* (2006.01)

(52) U.S. Cl.
CPC ......... *G01N 33/0047* (2013.01); *G01F 3/221* (2013.01); *G01F 3/222* (2013.01); *G01F 3/225* (2013.01)

(58) Field of Classification Search
CPC .......... G01F 3/221; G01F 3/222; G01F 3/225; G01N 33/0047
See application file for complete search history.

(56) References Cited

U.S. PATENT DOCUMENTS 5,439,178 A * 8/1995 Peterson ............... B05B 11/103 222/207
2018/0142684 A1* 5/2018 Abel ................... F04B 43/0045
2023/0324344 A1* 10/2023 Oshita ...................... G01N 5/02

* cited by examiner

*Primary Examiner* — Kathryn Elizabeth Limbaugh
(74) *Attorney, Agent, or Firm* — ScienBiziP, P.C.

(57) ABSTRACT

A gas sampling mechanism protecting an odor sensor and permeable membrane against direct exposure to the gas molecules of an external environment provides a one-way airflow, and includes an inlet chamber, a pump chamber connected to the inlet chamber, and a pump assembly connected to the pump chamber. The pump chamber can compress or evacuate air inside the pump chamber. An inlet valve is moveably arranged between the inlet chamber and the pump, and an outlet valve is movably arranged between the pump chamber and the ambient.

20 Claims, 5 Drawing Sheets

GAS SAMPLING MECHANISM AND GAS ANALYSIS DEVICE HAVING THE SAME

FIELD

The subject matter herein generally relates to fluid analysis, especially to a gas sampling mechanism and a gas analysis device having the same.

BACKGROUND

Molecular detection of odors is mainly realized by an odor sensor. A selective permeable membrane is applied on the odor sensor, and small volatile organic molecules can pass through the permeable membrane and be detected by the odor sensor.

In order to improve detecting efficiency of the small volatile organic molecules, it is necessary to open up and expose the odor sensor together with the permeable membrane to the environment which includes the odor/gas to be detected. However, the membrane and sensor may thus be polluted and even damaged.

BRIEF DESCRIPTION OF THE DRAWINGS

Implementations of the present technology will now be described, by way of example only, with reference to the attached figures.

DETAILED DESCRIPTION

Figure 1:
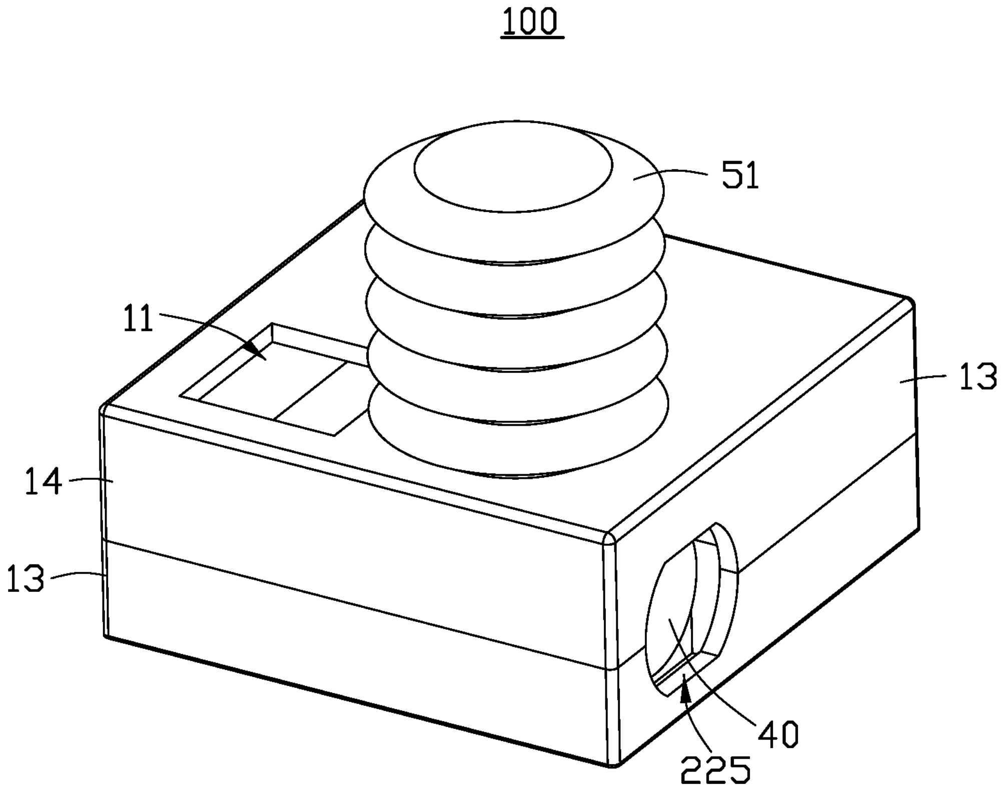
FIG. 1 is a diagrammatic view of a gas sampling mechanism according to an embodiment of the present disclosure.

It will be appreciated that for simplicity and clarity of illustration, where appropriate, reference numerals have been repeated among the different figures to indicate corresponding or analogous elements. In addition, numerous specific details are set forth to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to better illustrate details and features of the present disclosure.

The term “comprising,” when utilized, means “including, but not necessarily limited to”; it specifically indicates open-ended inclusion or membership in the so-described combination, group, series, and the like.

Referring to FIGS. 1-5, an embodiment of the present disclosure provides a gas sampling mechanism 100. The gas sampling mechanism 100 takes an airflow to an odor molecular detector 300. The gas sampling mechanism 100 is structured to protect the odor molecular detector 300 from contamination.

Figure 2:
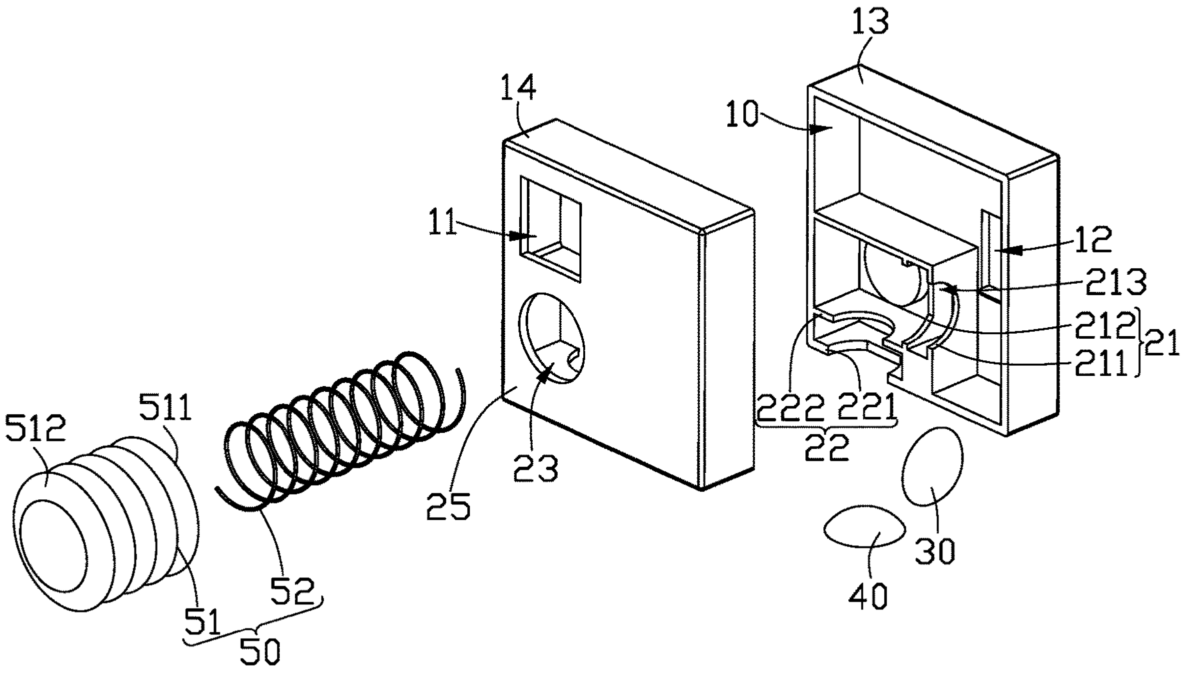
FIG. 2 is an exploded view of the gas sampling mechanism of FIG. 1.

Referring to FIGS. 1 and 2, the gas sampling mechanism 100 includes an inlet chamber 10, a pump chamber 20, an inlet valve 30, an outlet valve 40, and a pump assembly 50. The inlet chamber 10 communicates with the pump chamber 20. The pump assembly 50 is connected to the pump chamber 20. The inlet valve 30 is arranged between the inlet chamber 10 and the pump chamber 20. The outlet valve 40 is arranged on the pump chamber 20 and connected to an external environment. The inlet chamber 10 defines a first opening 11 and a second opening 12. The first opening 11 communicates with the external environment which carries gas molecules to be detected. The second opening 12 faces the odor molecular detector 300.

The pump assembly 50 can compress or evacuate air inside the pump chamber 20, so that the pump assembly 50 can drive air from the external environment into the pump chamber 20 through the first opening 11, and drive a portion of the air from the inlet chamber 10 towards the odor molecule detector 200 through the second opening 12. The odor molecule detector 200 detects odor molecules within the air and the concentration of the odor molecules. In at least one embodiment, the odor molecule detector 200 may be a volatile organic detector.

Figure 3:
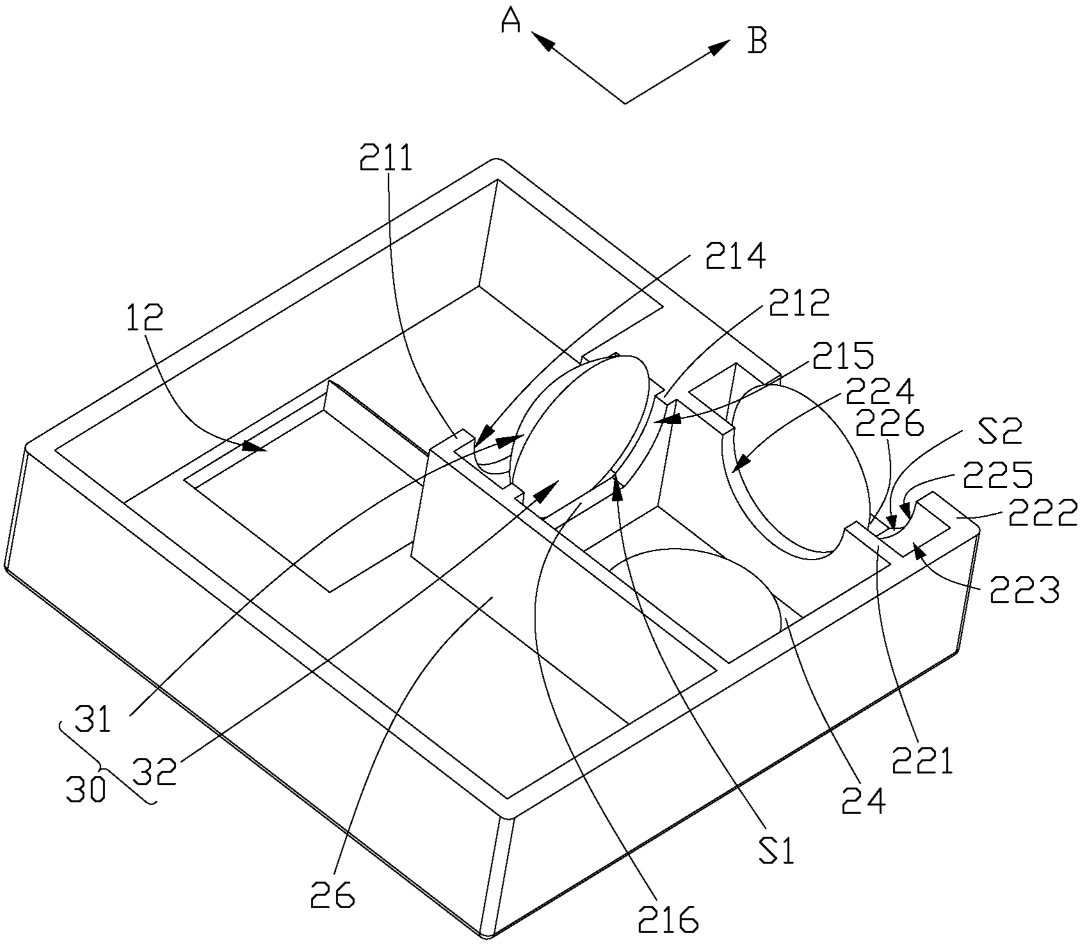
FIG. 3 is a pump structure of the gas sampling mechanism of FIG. 1, showing gas flows from an inlet chamber to a pump chamber.

Referring to FIGS. 2 and 3, the pump chamber 20 includes an entrance wall 21 and an exit wall 22. The entrance wall 21 includes a first plate 211 and a second plate 212 opposite to the first plate 211. The first plate 211 is spaced from the second plate 212 to form a first receiving space 213. The inlet valve 30 is movably arranged within the first receiving space 213. The first plate 211 defines a first through hole 214. The second plate 212 defines a second through hole 215. A first direction A is defined as a direction from the first plate 211 to the second plate 212. A projection of the first through hole 214 along the first direction A is within the inlet valve 30. A projection of the inlet valve 30 along the first direction A is within the second through hole 215. That is, a first gap S1 is formed between an outer surface of the inlet valve 30 and an inner surface of the second through hole 214. The inlet valve 30 is able to seal the first through hole 214, but not able to seal the second through hole 215.

Figure 4:
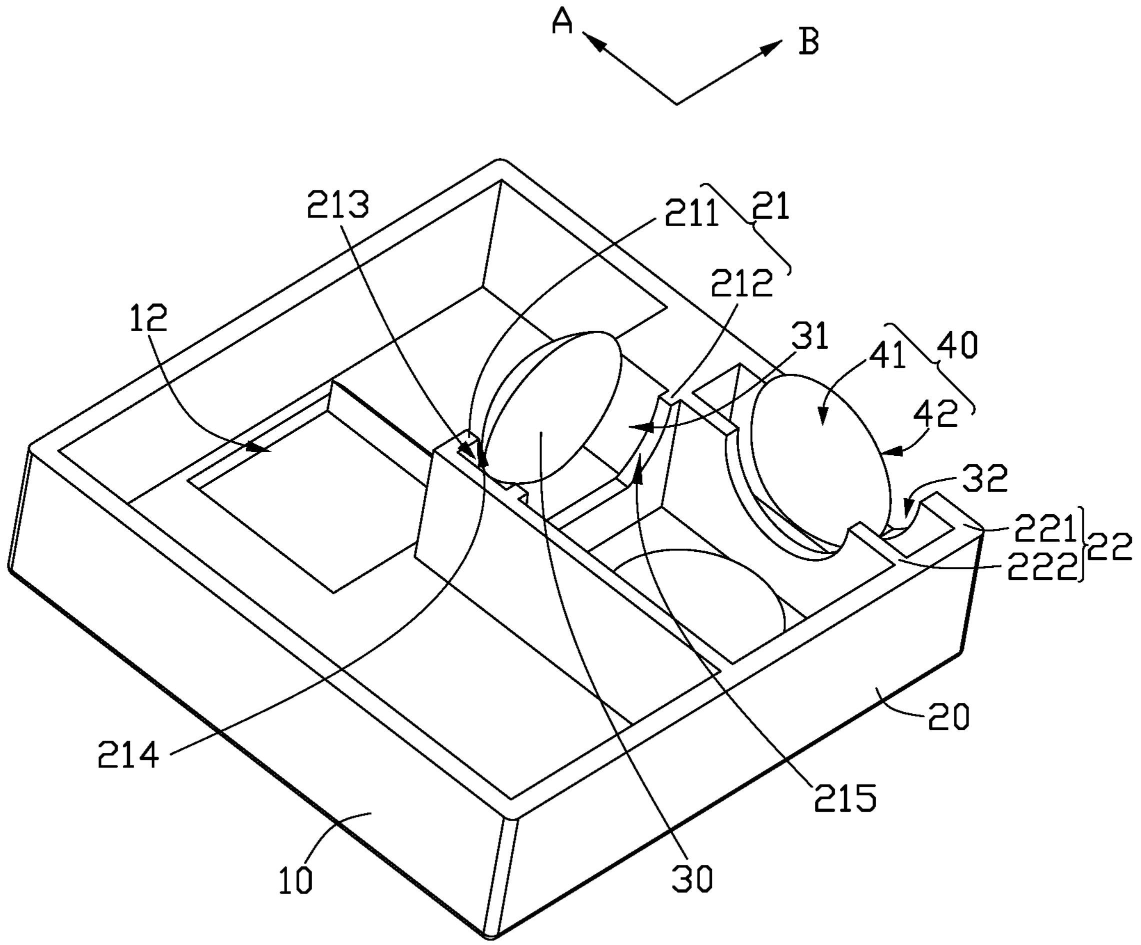
FIG. 4 is a similar to FIG. 3, but showing gas flows from the pump chamber to external environment.

Referring to FIGS. 3 and 4, the exit wall 22 includes a third plate 221 and a fourth plate 222 opposite to the third plate 221. The third plate 221 is spaced from the fourth plate 222 to form a second receiving space 223. The outlet valve 40 is movably arranged within the second receiving space 223. The third plate 221 defines a third through hole 224. The fourth plate 222 defines a fourth through hole 225. A second direction B is defined as a direction from the third plate 221 to the fourth plate 222. A projection of the third through hole 224 along the second direction B is within the outlet valve 40. A projection of the outlet valve 40 along the second direction B is within the fourth through hole 225. That is, a second gap S2 is formed between an outer surface of the outlet valve 40 and an inner surface of the fourth through hole 224. The outlet valve 40 can seal the third through hole 224, but cannot seal the fourth through hole 225.

When in use, the pump assembly 50 compresses air inside the pump chamber 20. Air flows from pump chamber 20 to the inlet chamber 10 through the second through hole 212 and the first through hole 211 successively, and the air pushes the inlet valve 30 towards the second through hole 214 until the inlet valve 30 seals the second through hole 215. Meanwhile, air flows from the pump chamber 20 to the external environment through the third through hole 224 and the fourth through hole 225 successively, and the air pushes the outlet valve 40 to move towards the fourth through hole 225. Because of the existing of the second gap S2, the outlet valve 40 cannot seal the fourth through hole 225, and the air inside the pump chamber 20 can flow freely to the external environment.

The pump assembly 50 can also create a vacuum inside the pump chamber 20. Air inside the inlet chamber 10 flows to the pump chamber 20 through the first through hole 214 and the second through hole 215 successively, and the air pushes the inlet valve 30 to move towards the second through hole 215. Because of the existing of the first gap S1, the inlet valve 30 cannot seal the second through hole 214, and the air can flow freely from the inlet chamber 10 to the pump chamber 20, and the pump assembly 50 can pull air from the external environment into the inlet chamber 10 through the first opening 11. Meanwhile, air from the external environment pushes the outlet valve 40 to move towards the third through hole 224 and seals the third through hole 224, so that air from the external environment cannot enter the pump chamber 20 through the fourth through hole 225 and the third through hole 224.

With the above configuration, air in the pump chamber 20, analogous to current in a diode, can flow in only one direction, which is out to the external environment, thereby providing unidirectional airflow to the odor molecular detector 300. Meanwhile, the air pump mechanism 100 can be configured to cover the odor molecular detector 300 and to protect the odor molecular detector 300 from being polluted and damaged.

Referring to FIGS. 3 and 4, in this embodiment, the entrance wall 21 further includes a first baffle 216. A portion of the second plate 212 extends inside the second through hole 215 to form the first baffle 216. A projection of the first baffle 216 along the first direction A is within the inlet valve 30. That is, the first baffle 216 can stop the inlet valve 30 from moving out of the first receiving space 213. The exit wall 22 further includes a second baffle 226. A portion of the fourth plate 222 extends inside the fourth through hole 225 to form the second baffle 226. A projection of the second baffle 226 along the second direction B is within the outlet valve 40. That is, the second baffle 226 can stop the outlet valve 40 from moving out of the second receiving space 22.

Referring to FIGS. 2, 3, and 4, in this embodiment, the first through hole 214 faces the second through hole 215 along the first direction A. Therefore, when air pressure inside the pump chamber 20 changes, the two pressures applied on each side of the inlet valve 30 are roughly collinear, so that the inlet valve 30 will move along the first direction A without shifting. The third through hole 224 faces the fourth through hole 22 along the second direction B. Therefore, when air pressure inside the pump chamber 20 changes, the two pressures applied on each side of the outlet valve 40 are roughly collinear, so that the outlet valve 40 will move along the second direction without shifting. In another embodiment, a rail (not shown) may be arranged inside the first receiving space 213 or the second receiving space 223. The rail is configured to guide the moving direction of the inlet valve 30 or the outlet valve 40.

Referring to FIGS. 2 and 3, in this embodiment, the inlet chamber 10 is L-shaped, and the pump chamber 20 is cuboid. The pump chamber 20 is connected to the inlet chamber 10 to form a cuboid. The inlet chamber 10 includes a box body 13 and a box cover 14 detachably connected to the box body 13. The box body 13 and the box cover 14 are matched to form the inlet chamber 10. The box cover 14 defines the first opening 11. The box body 13 defines the second opening 12. The pump chamber 20 further includes a bottom plate 24, a top plate 25, and a plurality of side plates 26. The bottom plate 24 is connected to a side of the box body 13. The side plate 26, the entrance wall 21, and the exit wall 22 are connected to a periphery of the bottom plate 24. The top plate 25 is connected to the box cover 14. The top late 25 defines a third opening 23. The pump assembly 50 is connected to the third opening 23.

Referring to FIGS. 1 and 2, in this embodiment, the pump assembly 50 includes an air squeezer 51 which is operated manually. The air squeezer 51 includes a blow nozzle 511 and an elastic cavity 512 connected to the blow nozzle 511. Air inside the elastic cavity 512 can be squeezed out from the blow nozzle 511. The blow nozzle 511 communicates with the third opening 23. In other embodiments, the pump assembly 50 may be an electric air compressor.

In this embodiment, the pump assembly 50 further includes a spring 52. One end of the spring 52 goes through the blow nozzle 511 and resists against the elastic cavity 512, and another end of the spring 52 goes through the third opening 23 and resists against the pump chamber 20. The spring 52 provides rebounding force returning the elastic cavity 512 to its original shape after being pressed.

Referring to FIGS. 3, and 4, in this embodiment, the inlet valve 30 is roughly petal-shaped. The inlet valve 30 includes a first surface 31 and a second surface 32 opposite to the first surface 31. The first surface 31 is convex away from the second surface 32, and the second surface 32 is concave toward the first surface 31. The first through hole 214 is arranged to correspond to the first surface 31, and the second through hole 215 is arranged to correspond to the second surface 32. Since the first surface 31 is convex, the first surface 31 can seal the first through hole 214, and a portion of the second surface 32 can be blocked by the first baffle 216. An inner surface of the second through hole 215 is spaced from a periphery of the second surface 32 to form the first gap S1, which allows air to pass through.

Figure 5:
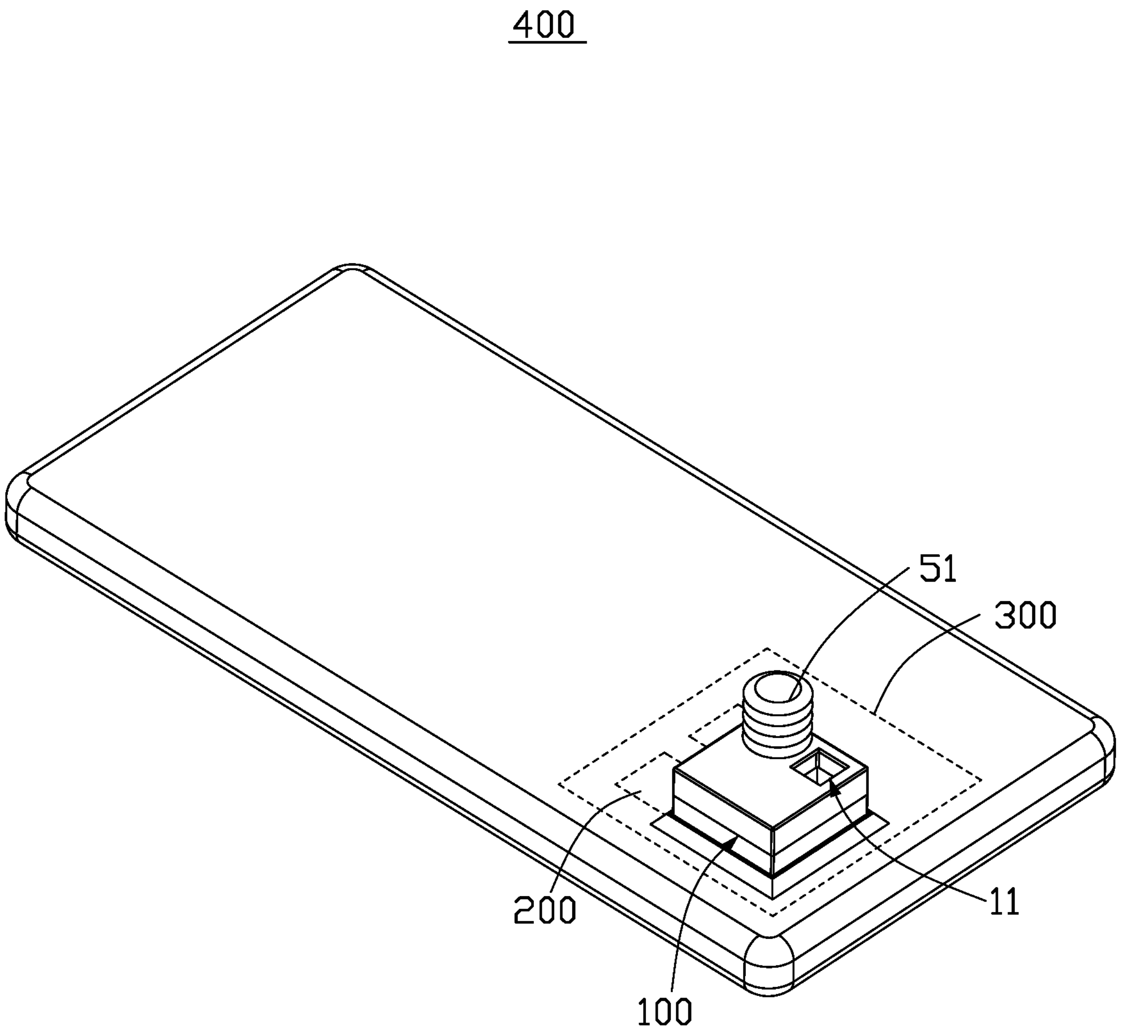
FIG. 5 is a diagrammatic view of a gas analysis device according to an embodiment of the present disclosure.

Referring to FIGS. 2 and 5, in this embodiment, the outlet valve 40 is roughly petal-shaped. The outlet valve 40 includes a third surface 41 and a fourth surface 42 opposite to the third surface 41. The third surface 41 is convex away from the fourth surface 42, and the fourth surface 42 is concave toward the third surface 41. The third through hole 224 corresponds to the third surface 41, and the fourth through hole 225 corresponds to the fourth surface 42. Since the third surface 41 is convex, the convexity can seal the third through hole 224, and a portion of the fourth surface 42 can be blocked by the second baffle 226. An inner surface of the fourth through hole 225 is spaced from a periphery of the fourth surface 42 forming the second gap S2, which allows gas to pass through.

Referring to FIGS. 2 and 5, the embodiment also provides a gas analysis device 400. The gas analysis device 400 includes a selective permeable membrane 200, an odor molecular detector 300, and the gas sampling mechanism 100. The selective permeable membrane 200 is arranged on the odor molecular detector 300, and the selective permeable membrane 200 is arranged to correspond to the second opening 12. Specifically, the gas analysis device 400 can be incorporated into a mobile phone, a smart watch, etc.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. A gas sampling mechanism comprising:

an inlet chamber;

a pump chamber connected to the inlet chamber;

a pump assembly connected to the pump chamber, and configured to compress or expand air inside the pump chamber;

an inlet valve movably arranged between the inlet chamber and the pump chamber; and an outlet valve movably arranged between the pump chamber and an external environment;

wherein the inlet chamber defines a first opening and a second opening, the first opening communicates with the external environment, the second opening is configured to communicate with an odor molecular detector;

the pump chamber comprises an entrance wall and an exit wall, the entrance wall comprises a first plate and a second plate spaced from the first plate, the first plate defines a first through hole, the second plate defines a second through hole, the exit wall comprises a third plate and a fourth plate spaced from the third plate, the third plate defines a third through hole, the fourth plate defines a fourth through hole, the second through hole is arranged between the first through hole and the second opening;

the inlet valve is movably arranged between the first plate and the second plate, a first direction is defined as a direction from the first plate to the second plate, a projection of the first through hole along the first direction falls within the inlet valve, a projection of the inlet valve along the first direction falls within the second through hole;

the outlet valve is movably arranged between the third plate and the fourth plate, a second direction is defined as a direction from the third plate to the fourth plate, a projection of the third through hole along the second direction falls within the outlet valve, a projection of the outlet valve falls within the fourth through hole.

2. The gas sampling mechanism of claim 1, wherein the pump assembly comprises an air squeezer, the air squeezer comprises a blow nozzle and an elastic cavity connects to the blow nozzle, the pump chamber defines a third opening, the blow nozzle communicates with the third opening.

3. The gas sampling mechanism of claim 2, wherein the pump assembly further comprises a spring, an end of the spring goes through the blow nozzle and resists against the elastic cavity, another end of the spring goes through the third opening and resists against the pump chamber.

4. The gas sampling mechanism of claim 1, wherein the entrance wall further comprises a first baffle, a portion of the second plate extends into the second through hole to form the first baffle, a projection of the first baffle along the first direction is within the inlet valve.

5. The gas sampling mechanism of claim 1, wherein the exit wall further comprises a second baffle, a portion of the fourth plate extends into the fourth through hole to form the second baffle, a projection of the second baffle along the second direction is within the outlet valve.

6. The gas sampling mechanism of claim 1, wherein the first through hole faces the second through hole, and the third through hole faces the fourth through hole.

7. The gas sampling mechanism of claim 1, wherein the pump chamber further comprises a box body and a box cover detachably connected to the box body, the box cover defines the first opening, the box body defines the second opening.

8. The gas sampling mechanism of claim 7, wherein the pump chamber further comprises a bottom plate, a top plate, and a plurality of side plates, the bottom plate is connected to the box body, the top plate is connected to the box cover, the plurality of side plates, the entrance wall, and the exit wall are connected to a periphery of the bottom plate, the top plate defines the third opening.

9. The gas sampling mechanism of claim 1, wherein the inlet valve comprises a first surface and a second surface, the first surface is convex away from the second surface, the second surface is concave toward the first surface, the first through hole faces the first surface, and the second through hole faces the second surface.

10. The gas sampling mechanism of claim 1, wherein the outlet valve comprises a third surface and a fourth surface, the third surface is convex away from the fourth surface, the fourth surface is concave toward the third surface, the third through hole faces the third surface, and the fourth through hole faces the fourth surface.

11. A gas analysis device comprising:

an odor molecular detector;

a selective permeable membrane covers the odor molecular detector; and a gas sampling mechanism covers the selective permeable membrane;

wherein the gas sampling mechanism comprises:

an inlet chamber defining a first opening and a second opening, the first opening communicates with the external environment, the second opening is configured to face the selective permeable membrane;

a pump chamber comprising an entrance wall and an exit wall, the entrance wall comprises a first plate and a second plate spaced from the first plate, the first plate defines a first through hole, the second plate defines a second through hole, the exit wall comprises a third plate and a fourth plate spaced from the third plate, the third plate defines a third through hole, the fourth plate defines a fourth through hole, the second through hole is arranged between the first through hole and the second opening;

an inlet valve is movably arranged between the first plate and the second plate, a first direction is defined as a direction from the first plate to the second plate, a projection of the first through hole along the first direction falls within the inlet valve, a projection of the inlet valve along the first direction falls within the second through hole;

an outlet valve movably arranged between the third plate and the fourth plate, a second direction is defined as a direction from the third plate to the fourth plate, a projection of the third through hole along the second direction falls within the outlet valve, a projection of the outlet valve falls within the fourth through hole.

12. The gas analysis device of claim 11, further comprising a pump assembly, wherein the pump assembly comprises an air squeezer, the air squeezer comprises a blow nozzle, and an elastic cavity connects to the blow nozzle, the pump chamber defines a third opening, the blow nozzle communicates with the third opening.

13. The gas analysis device of claim 12, wherein the pump assembly further comprises a spring, an end of the spring goes through the blow nozzle and resists against the elastic cavity, another end of the spring goes through the third opening and resists against the pump chamber.

14. The gas analysis device of claim 11, wherein the entrance wall further comprises a first baffle, a portion of the second plate extends inside the second through hole to form the first baffle, a projection of the first baffle along the first direction is within the inlet valve.

15. The gas analysis device of claim 11, wherein the exit wall further comprises a second baffle, a portion of the fourth plate extends inside the fourth through hole to form the second baffle, a projection of the second baffle along the second direction is within the outlet valve.

16. The gas analysis device of claim 11, wherein the first through hole faces the second through hole, and the third through hole faces the fourth through hole.

17. The gas analysis device of claim 11, wherein the pump chamber further comprises a box body and a box cover detachably connected to the box body, the box cover defines the first opening, the box body defines the second opening.

18. The gas analysis device of claim 17, wherein the pump chamber further comprises a bottom plate, a top plate, and a plurality of side plates, the bottom plate is connected to a side of the box body, the top plate is connected to a side of the box cover, the plurality of side plates, the entrance wall, and the exit wall are connected to a periphery of the bottom plate, the top plate defines the third opening.

19. The gas analysis device of claim 11, wherein the inlet valve comprises a first surface and a second surface, the first surface is convex away from the second surface, the second surface is concave toward the first surface, the first through hole faces the first surface, and the second through hole faces the second surface.

20. The gas analysis device of claim 11, wherein the outlet valve comprises a third surface and a fourth surface, the third surface is convex away from the fourth surface, the fourth surface is concave toward the third surface, the third through hole faces the third surface, and the fourth through hole faces the fourth surface.

* * * * *